US007005982B1

(12) United States Patent
Frank

(10) Patent No.: US 7,005,982 B1
(45) Date of Patent: Feb. 28, 2006

(54) CARRIER SECURITY SYSTEM

(76) Inventor: David L. Frank, 2701 S. Ocean Blvd., Highland Beach, FL (US) 33487

(*) Notice: Subject to any disclaimer, the term of this patent is extended or adjusted under 35 U.S.C. 154(b) by 0 days.

(21) Appl. No.: 10/280,255

(22) Filed: Oct. 25, 2002

Related U.S. Application Data

(60) Provisional application No. 60/347,997, filed on Oct. 26, 2001.

(51) Int. Cl.
*G08B 1/08* (2006.01)

(52) U.S. Cl. ........................... 340/539.26; 340/539.17; 436/57

(58) Field of Classification Search ........... 340/539.26, 340/539.1, 539.13, 539.17, 692; 436/58, 436/63, 57
See application file for complete search history.

(56) References Cited

U.S. PATENT DOCUMENTS 4,428,907 A * 1/1984 Heijenga et al. .............. 422/61
5,328,847 A * 7/1994 Case et al. .................. 205/778
5,874,046 A * 2/1999 Megerle .................... 422/68.1
5,923,421 A * 7/1999 Rajic et al. ................. 356/328
5,935,862 A * 8/1999 Novak ........................ 436/104
6,031,455 A * 2/2000 Grube et al. ........... 340/539.26
6,228,657 B1 * 5/2001 Genovese et al. .......... 436/167
6,741,174 B1 * 5/2004 Rhoades et al. ............ 340/540

* cited by examiner

*Primary Examiner*—Phung T. Nguyen
(74) *Attorney, Agent, or Firm*—Jose Gutman; Fleit, Kain, Gibbons, Gutman, Bongini & Bianco P.L.

(57) ABSTRACT

A process deploys detection devices in the carrier vehicles, collection facilities and collection boxes to determine if hazardous materials have deposited. The system is designed to provide detection, identification and measurement of chemical, biological and DNA/RNA elements. When a hazardous material is detected, an alarm notifies the worker. The system communicates with a central monitoring station that receives vehicle ID, GPS positioning and identification of the hazardous material. A HAZMAT team is then dispatched to the vehicle site. Systems that can benefit include carrier vehicles, collection boxes, collection facilities, mail carriers, cargo carriers, freight carriers, package delivery services, express delivery services, etc. The carrier vehicles may include trucks, automobiles, aircraft and ships. The collection boxes may include, containers, mail collection boxes, express delivery collection boxes, etc. The collection facilities may include mail and package receiving centers, express mail and package receiving stations, and shipping and receiving stations.

37 Claims, 12 Drawing Sheets

500

600

700

900

1200

| 1202 | 1204 | 1206 | 1208 | 1210 |
|------|------|------|------|------|
| Header | Alarm Message 1 | Alarm Message 2 | Alarm Message 3 | Alarm Message 4 |

1212

Vehicle ID: 20045
Hazmat: Anthrax
T/D: 14:01 / 10-02-02
GPS: 12.

CARRIER SECURITY SYSTEM

CROSS-REFERENCE TO RELATED APPLICATIONS

This application is based upon and claims priority from prior U.S. Provisional Patent Application No. 60/347,997, filed on Oct. 26, 2001, the entire disclosure of which is herein incorporated by reference.

BACKGROUND OF THE INVENTION

1. Field of the Invention

This invention relates in general to security and remote monitoring systems, and more particularly to a monitoring system for use as a security system for detecting and identifying biological, chemical, DNA and radioactive hazardous materials within carrier receptacles and carrier vehicles.

2. Description of Related Art

Current attempts at providing hazardous material detection within a delivery system are limited to chemical detection systems located at carrier facilities. New attempts at launching chemical detection systems are focused on the mail, cargo, and package sorting machines where the chemical or biological contaminants are dislodged and disseminated across the sorting facility and numerous packages. The resulting action when a contaminant is detected is typically the closure of the facility. The source of the contaminated mail, cargo or packages and the carrier personnel that delivered the contaminated materials are not identified by these systems. The carrier personnel within the sorting facilities are protected by evacuating the facility such as when an audible alarm is sounded and/or a visual alarm is visually indicated.

These systems do not provide the field personnel with an alarm to indicate that they have been exposed during mail, cargo or package pickup and delivery. The current systems do not prevent contaminants from entering the carrier facility and do not protect the carrier facility or carrier assets. The closure of a carrier facility is a very costly event. Postal facilities closed by the Anthrax contamination of 2001 are not expected to be re-opened for an extended period of time.

Therefore a need exists to overcome the problems with the prior art as discussed above, and particularly for a monitoring system for use as a security system for detecting and identifying biological, chemical, DNA and radioactive hazardous materials within carrier receptacles and carrier vehicles.

SUMMARY OF THE INVENTION

The present invention provides a method of detecting and identifying hazardous material within mail, cargo or packages before they can be delivered to the carrier facility or as they are presented at the collection facility. This provides for the protection of carrier facilities, personnel, assets and the general public. The present invention also provides a method of alarming the carrier in the field that a hazardous material has been identified within the collection box or within the carrier vehicle.

The present invention also provides a method of alerting the authorities that a contaminant has been identified at a specific location at a specific date and time to allow the authorities to take the appropriate actions.

Additionally, the present invention provides a method of eliminating biological agents from mail sorting machines so that the dissemination of a contaminant across a large number of mail, packages or containers is avoided.

DESCRIPTION OF THE PREFERRED EMBODIMENTS

A preferred embodiment of the present invention focuses on preventing hazardous materials from entering the carrier facility to avoid the closure of the building and notifies workers in the field of potential exposure.

A preferred embodiment of the present invention preferably provides for the detection and identification of chemical, biological, DNA and radioactive materials, such as explosives, biological agents and viruses, within the collection/delivery vehicles, collection boxes and collection facilities with local alarms and communications capabilities to notify authorities. A preferred embodiment of the present invention also determines if hazardous materials have been collected on the route or at the collection facility. A monitoring facility receives the alarms generated from the detection and identification systems within the mail carrier vehicles and collection boxes.

The detection and identification technology associated with present invention preferably would be provided in two phases to expedite deployment. In the first phase the carrier vehicles would be tested as they approach the carrier facility to prevent the hazardous materials from entering the facility.

A central monitoring facility could monitor the testing across the region or nation. In phase two, a real-time detection device would notify the carrier worker that a hazardous material has been collected while on the route or at the collection facility. An alarm notifies the worker that a hazardous material is present. The system communicates with a central monitoring station that receives vehicle ID, GPS positioning and identification of the hazardous material. A HAZMAT team is then dispatched to the site.

Figure 1:
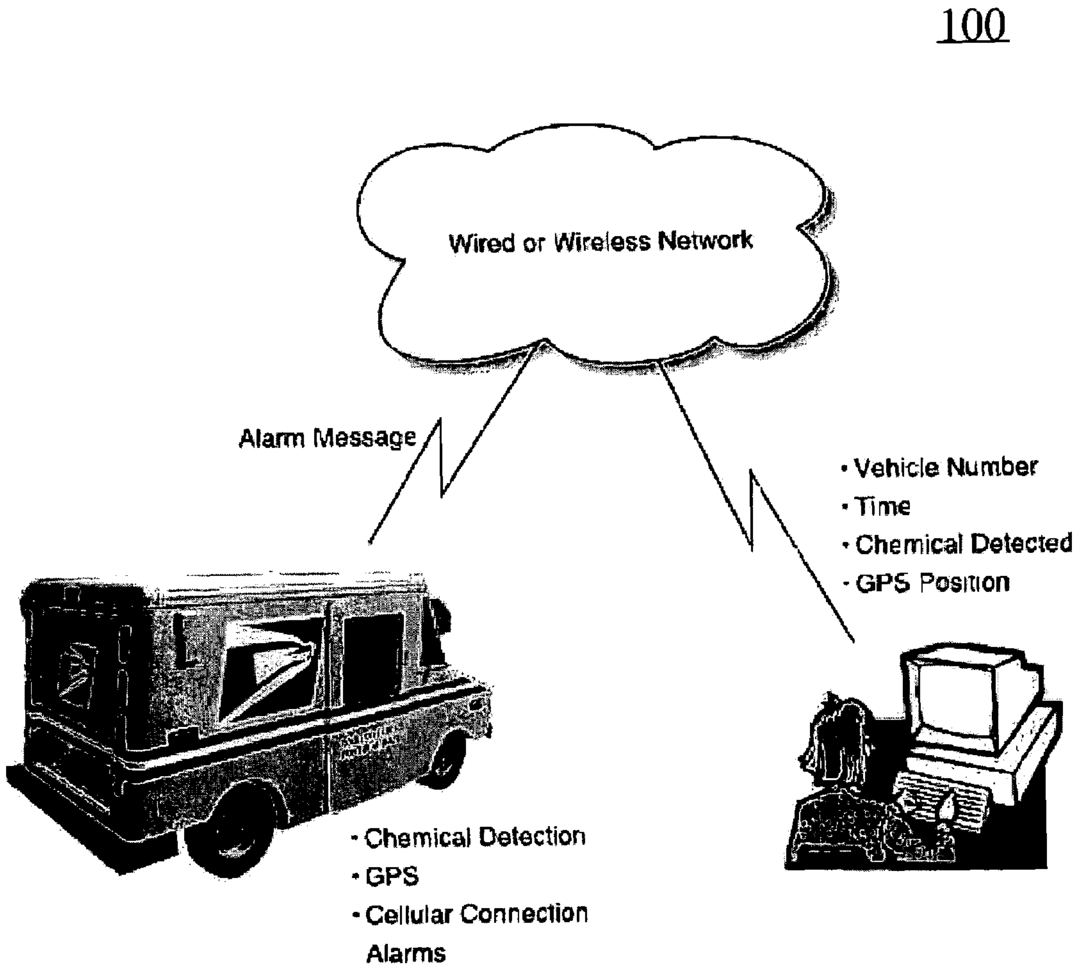
FIG. 1 is a block diagram illustrating a carrier security system in accordance with a preferred embodiment of the present invention.

A preferred embodiment includes a system that preferably is comprised of the following elements:

- Monitoring Facility
- Real-Time Verification System
  - Carrier Vehicle
  - Collection Facility
  - Collection Box
- Verification Station
- Static Detection System
  - Carrier Vehicle
  - Collection Facility
  - Collection Box An overview of an exemplary carrier security system is illustrated in FIG. 1. Also, as shown in FIG. 11, the detection and identification technologies associated with the present invention are designed in a tiered approach.

Figure 11:
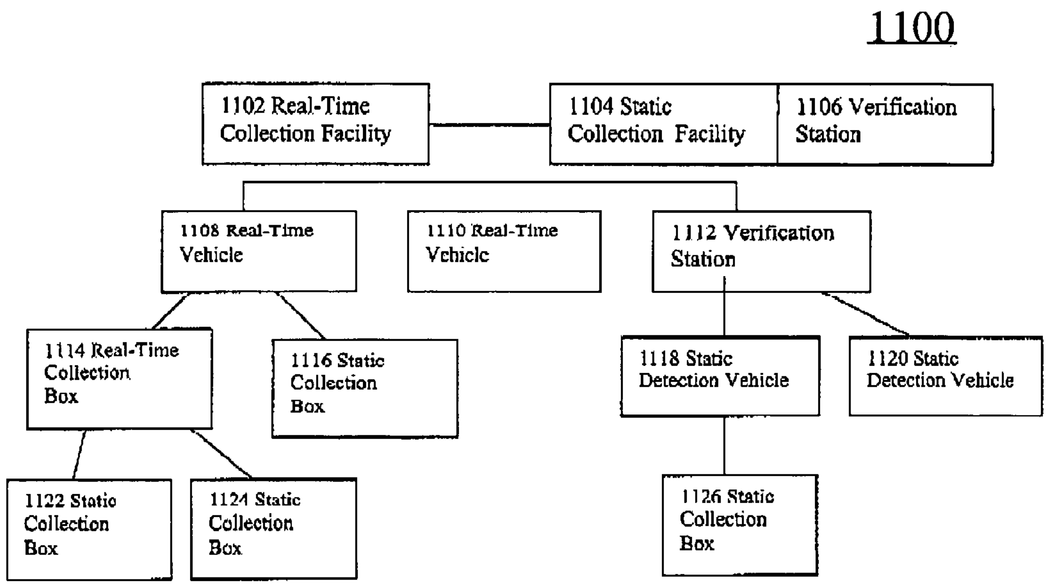
FIG. 11 is a chart illustrating a tiered design of carrier detection system elements as described in a preferred embodiment of the present invention.

Referring to FIG. 11, Static Devices utilize an air sampling and filter system. A self-sealing removable filter is provided to ensure the safety of the personnel removing and testing the sample filter. The filter is tested using a chemical and biological detection capabilities.

Real-Time Devices provide a real-time detection device that can notify the worker that a hazardous material has been detected immediately. These devices are used to support the static detection devices. A port is provided on the real-time device for analysis of a filter from a static device.

Real-Time collection facilities 1102 provide automated detection systems. Static collection systems 1104 require the use of a verification station 1106 or support of a real-time detection system 1102.

Real Time Vehicle systems 1108 provide automated detection systems. Real-time vehicle systems 1108 can support static collection boxes 1116.

Verification stations 1112 can support static detection systems deployed in vehicles 1118 or collection boxes 1126.

1.0 Central Monitoring Station

Figure 8:
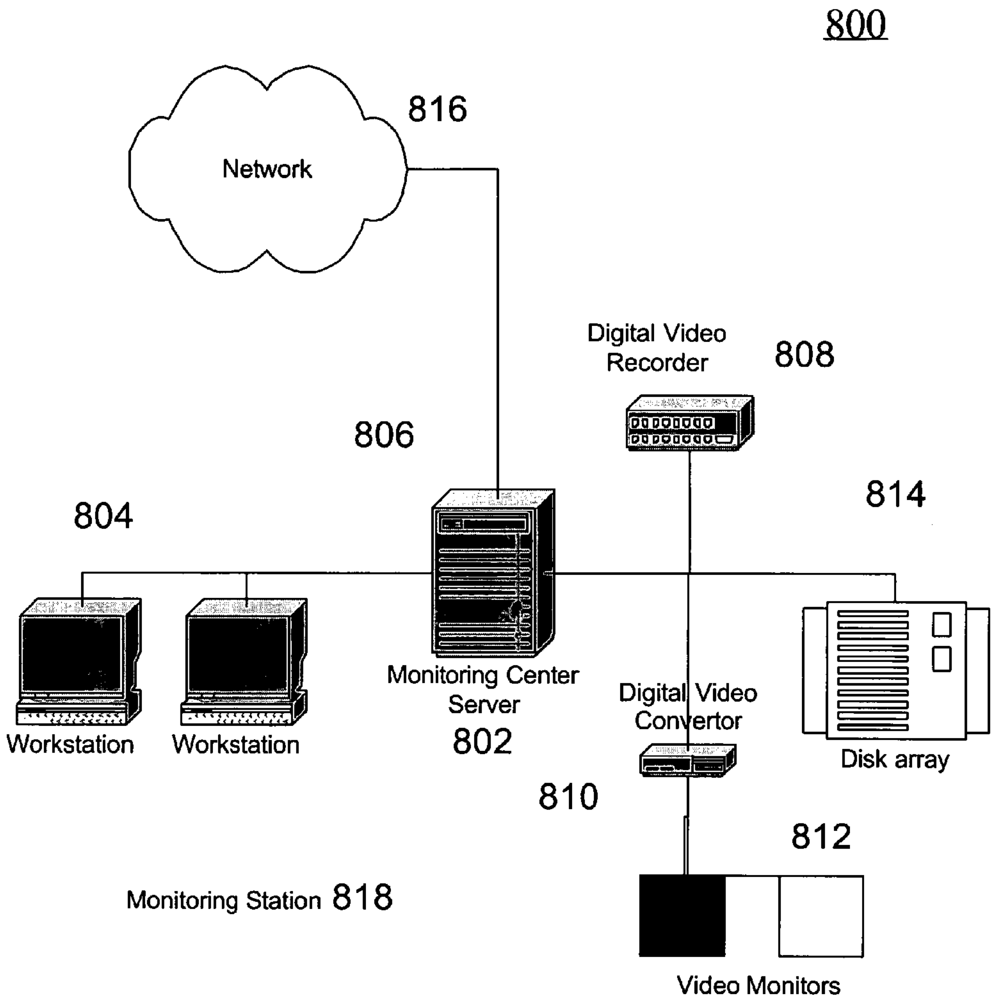
FIG. 8 is a more detailed block diagram showing a monitoring station as described in a preferred embodiment of the present invention.

The central monitoring station, as shown in FIG. 8, receives alarms from the detection systems deployed in such locations as vehicles, collection boxes and verification stations. When the detection system identifies a hazardous material, an alarm is transmitted via a data network to the central monitoring station. The alarm is transmitted across media such as wireless, wire-line or satellite communications to one or more computers at the central monitoring station. The alarm message provides an identification number of the detection device, the GPS positioning of the detection device, the time and date that the hazardous material was detected and identifies the hazardous material.

The central monitoring station is connected to database information describing the shipping data associated with all mail, parcels or containers within the vehicle, collection box, or facility that has been identified in the alarm message.

The central monitoring station has communications access to hazardous materials agencies that are responsible for addressing the alarm. The local detection station and the central monitoring station comprise an alarm notification system for contacting authorities and personnel to alert the responsible parties of the incident.

Referring to FIG. 8, the monitoring system is comprised of a server 802 that provides access to the Carrier Security System application, communications network 816, and local network peripheral devices such as: work stations for monitoring personnel 804, digital storage devices 814, digital video converters 810, digital video recorders 808 and video monitors 812. Additional devices can be added to the local area network and can be supported by the server 806.

When a carrier detection system recognizes an alarm, the carrier detection system contacts the monitoring station and sends an alarm message. The alarm data provides the GPS positioning, the hazardous material identification and measurement, the time and date and the carrier security system identification number. If the carrier security system is equipped with a video camera, digital video is transmitted to the monitoring station. If the carrier security system is equipped with a video recording device, video events, especially those associated with an alarm condition, are recorded and can be downloaded to the monitoring station.

2.0 Real-Time Evaluation Systems

Figure 2:
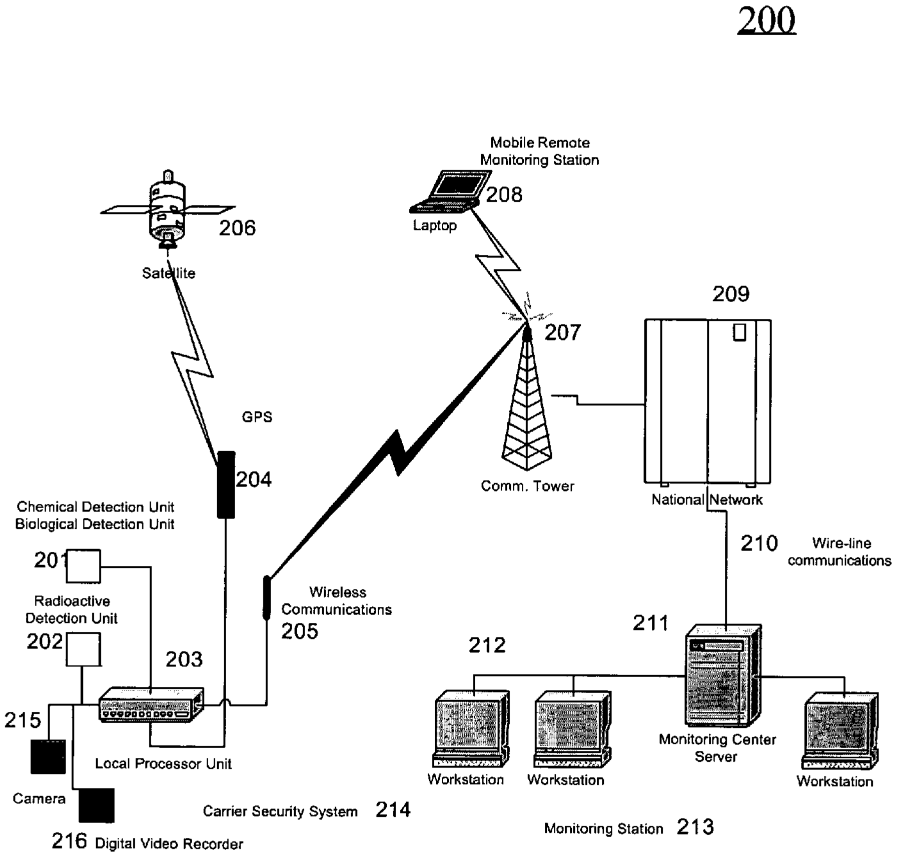
FIG. 2 is a block diagram illustrating a real-time detection system in accordance with a preferred embodiment of the present invention.
Figure 4:
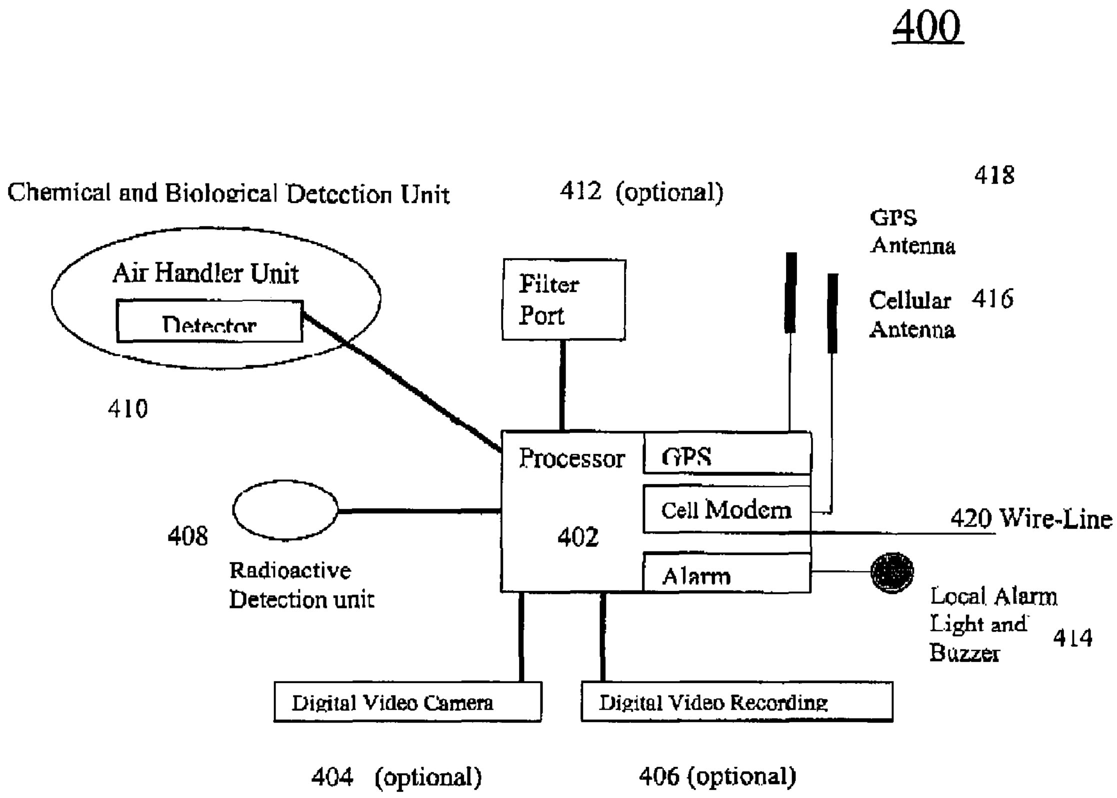
FIG. 4 is a more detailed block diagram showing a real-time detection system, according to a preferred embodiment of the present invention.

The real-time evaluation systems, as shown in FIGS. 2 and 4, are equipped with processors that provide the base capabilities for detection and analysis of unauthorized element(s), alarm generation, wireless communications, GPS positioning, and video surveillance capabilities.

The detection devices provide real-time analysis for chemical, biological and radioactive detection and identification of elements. These elements when detected in carrier storage environments may comprise unauthorized elements that the system alerts (and/or alarms) authorities and personnel to take appropriate actions.

The real-time detection systems also provide verification ports for filters used in the Static Detection systems. For example, a real-time evaluation system in a carrier vehicle could also be used to verify static detection systems deployed in collection boxes prior to releasing the contents of the box.

FIG. 2 provides a block diagram of the carrier security system deployed as a real-time detection system. The chemical and biological detection unit 201 provides continuous monitoring of the air and the elements within the detection area. The radioactive detection unit 202 provides continuous monitoring for radioactive elements. The local processor unit 203 analyzes the inputs from the chemical, biological and radioactive detection units to determine if an alarm condition is present. The GPS antenna 204 connects the GPS processing within the local processor 203 to identify the current position of the carrier security system. The GPS satellite 206 provides information to the GPS processor within the local processor to provide the positioning information. The wireless antenna 205 provides connectivity for the data and video transmission unit located within the local processor 203. The radio tower 207 connects the wireless transmission from the carrier security system local processor 203 to the national network. The national network 209 provides connectivity between the carrier security system 214 and the monitoring station 213. The server at the monitoring station 211 provides access to the carrier security system applications communications link 210 and connects the workstations 212. The workstations provide access for the monitoring personnel to access the system, receive alarms and alarm data, to access video images, and respond to the reported alarms. When a detection device 201, 202 detects a hazardous material, the local processor 203 recognizes the alarm, identifies the hazardous materials, quantifies the hazardous materials and generates an alarm message. The wireless processor within the local processor sends an alarm message over the wireless link 205. The alarm data provides the GPS positioning obtained through the GPS antenna 204 and GPS processor 203, the hazardous material identification and measurement 201, 202, 203, the time and date and the carrier security system identification number. If the carrier security system is equipped with a video camera 215, digital video is transmitted to the monitoring station 213. If the carrier security system is equipped with a video recording device 216, video events are recorded.

2.1 Vehicle System

Real-time detection devices in carrier vehicles provide the capability to determine if hazardous materials such as chemicals, explosives, biological agents, or radioactive materials have deposited into the vehicle as the mail, cargo, packages etc. are collected. When a hazardous material is detected, an alarm notifies the driver to exit the vehicle. The system communicates with a central monitoring station that receives vehicle ID, GPS positioning and identification of the hazardous material. A HAZMAT team is then dispatched to the vehicle site. Should digital video surveillance equipment be deployed in the vehicle, remote video monitoring is utilized by central monitoring and the local HAZMAT team.

The real-time detection systems also provide verification ports for filters used in the Static Detection systems. For example, a real-time evaluation system in a carrier vehicle could also be used to verify static detection systems deployed in collection boxes prior to releasing the contents of the box.

2.2 Collection Facility

Real-time detection devices in carrier facilities provide the capability to determine if hazardous materials such as chemicals, explosives, biological agents, or radioactive materials are being deposited as mail, cargo, packages etc. at the facility. Protective staging areas are provided for the incoming mail, cargo, packages, etc. When a hazardous material is detected, an alarm notifies the workers at the facility. The system communicates with a central monitoring station that receives vehicle ID, GPS positioning and identification of the hazardous material. A HAZMAT team is then dispatched to the vehicle site. Should digital video surveillance and recording equipment be deployed in the vehicle, video history files may be able to provide important data to the investigation team.

The real-time detection systems also provide verification ports for filters used in the Static Detection systems. For example, a real-time evaluation system in a carrier vehicle could also be used to verify static detection systems deployed in collection boxes prior to releasing the contents of the box.

2.3 Collection Box

Real-time detection devices in collection boxes provide the capability to determine if hazardous materials such as chemicals, explosives, biological agents, or radioactive materials have deposited into the collection box as the mail, cargo, packages etc. are collected. When a hazardous material is detected, an alarm notifies workers. The system communicates with a central monitoring station that receives vehicle ID, GPS positioning and identification of the hazardous material. A HAZMAT team is then dispatched to the vehicle site. Should digital video surveillance and recording equipment be deployed in the vehicle, video history files may be able to provide important data to the investigation team.

The real-time detection systems also provide verification ports for filters used in the Static Detection systems. For example, a real-time evaluation system in one collection box may support a number of other collection boxes in the area. The collection box with the real-time detection system can be used to verify filters from static detection systems.

Figure 7:
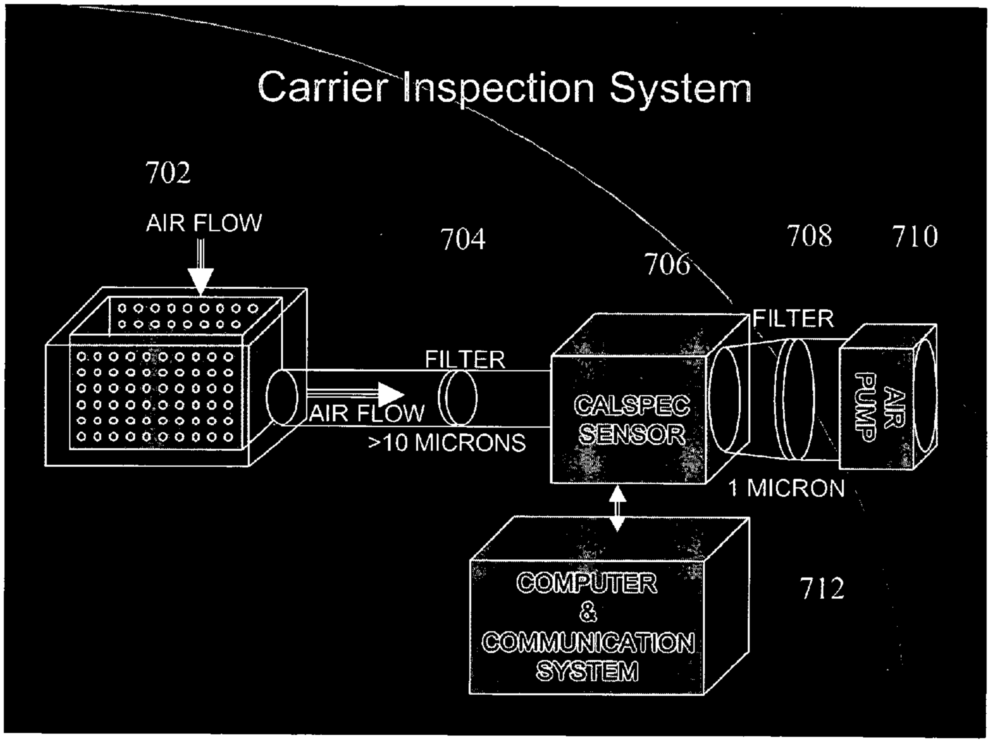
FIG. 7 is a more detailed block diagram showing a real-time detection according to a preferred embodiment of the present invention.

FIG. 7 provides a block diagram of an exemplary real-time detection system. A filter 704 of a pre-determined value, such as 10 microns, clears elements from the air handler unit 702. The sensor device 706 could be a Calspec tester, a mass spectrometer, etc. The computer device 712 analyzes the output from the sensor 706 to detect, identify and measure the elements paced in the sensor device. The outer filter 708 traps the elements passing through the tester. The air pump 710 pulls the air through the system to enable the analysis. When a detection device 706 detects a hazardous material, the local processor 712 recognizes the alarm, identifies the hazardous materials, quantifies the hazardous materials provides a local alarm and generates a local alarm message. The communications device 712 sends an alarm message. The alarm data provides the GPS positioning, the hazardous material identification and measurement, the time and date and the carrier security system identification number.

3.0 Static Detection Systems

Static detection systems use air handling systems and filters to trap evidence of hazardous materials. The filters are tested at verification stations to determine if any hazardous materials are present.

Self-Sealing Filters are used to protect the personnel from contamination. The filters deployed in static detection systems have an exposed handle to grab and pull the filter out of the static air handler. As the filter is removed, a film attaches and seals the filter area.

Figure 3:
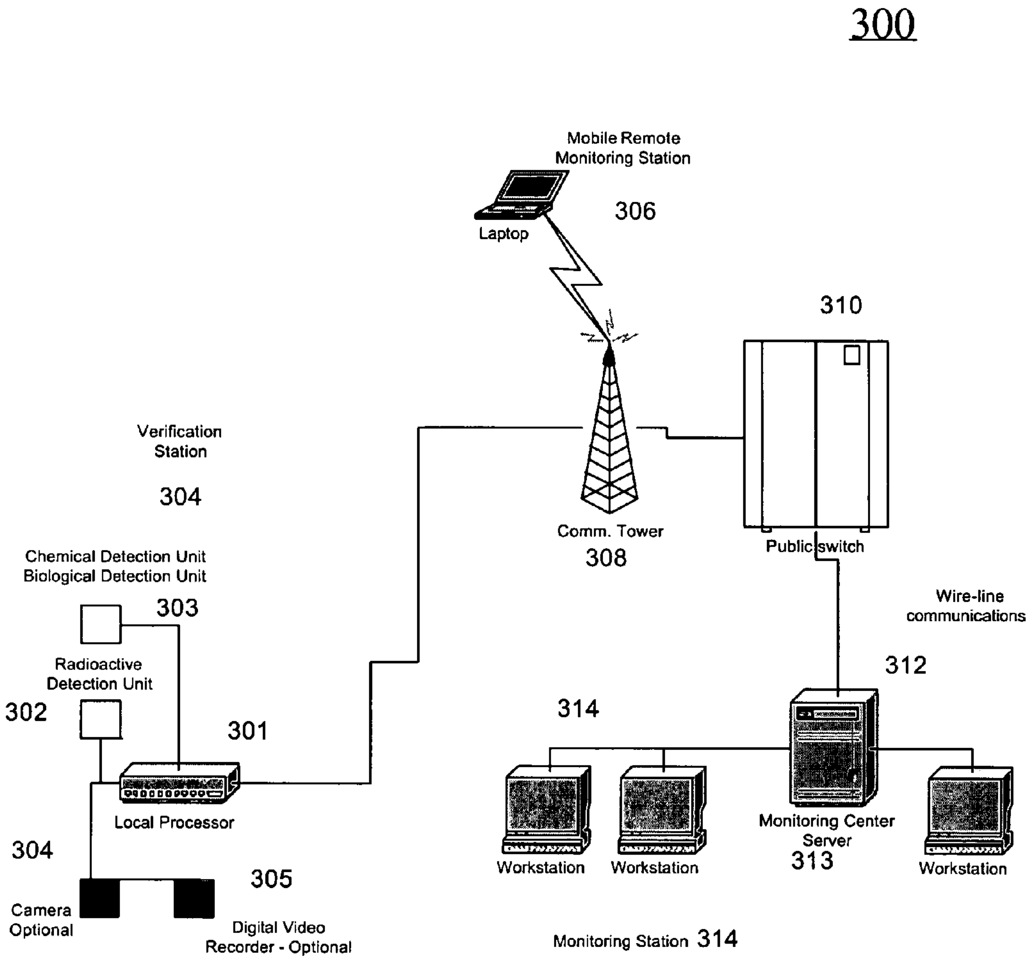
FIG. 3 is a more detailed block diagram showing a static detection system, according to a preferred embodiment of the present invention.

FIG. 3 provides an overview of an exemplary detection system. With reference to FIGS. 3 and 2, a detection system could be deployed in vehicle systems, collection facilities and collection boxes. The chemical and biological detection unit 303 provides continuous monitoring of the air and the elements analyzed across the filters subjected to testing. The radioactive detection unit 302 provides continuous monitoring for radioactive elements analyzed across the filters subjected to testing. The local processor unit 301 analyzes the inputs from the chemical, biological and radioactive detection units to determine if an alarm condition is present. An optional GPS antenna 204 (such as shown in FIG. 2) connects with the GPS processing within the local processor 301 to identify the current position of the carrier security system. The GPS satellite 206 provides information to the GPS processing within the local processor 301 to provide the positioning information. Alternatively, the location information may be predefined for a particular local processor 301 in the system, such as in a station in the system. An exemplary communication link, such as a dial-up phone line or a dedicated line, provides connectivity for the data and video transmission unit located within the local processor 301. For wireless communication links, the radio tower communication system 308 connects a wireless transmission from the carrier security system local processor 301 to a national network interface (such as shown in FIG. 2). The dial-up phone line or dedicated line is communicatively coupled with a public switched telephone network (PSTN) 310 that provides connectivity between the carrier security system station 304 and the monitoring center server 313. The monitoring server 313 communicates via wireline communications interface 312 with the monitoring station 304 in the carrier security system (via the PSTN) and also provides applications communications with the workstations 314. The workstations 314 provide access for the monitoring personnel to access the system and applications, such as to receive alarms and alarm data, to access video images, and to respond to the reported alarms. When a detection device 301, 302 detects a hazardous material, the local processor 301 recognizes the alarm, identifies the hazardous materials, quantifies the hazardous materials and generates an alarm message. The local processor sends an alarm message over the communications link to the monitoring center server 313. The alarm data, for example, provides the location of the verification station 304 such as via the GPS positioning obtained through the GPS antenna 204 and GPS processin in the local processor 301, the hazardous material identification and measurement 301, 302, 303, the time and date, and the carrier security system identification number. If the carrier security system is equipped with a video camera 304, 305, digital video is transmitted (either real-time and/or store-n-forward) to the monitoring station 313. In particular note that if the carrier security system is equipped with a video recording device 305, video events are recorded and further could be remotely monitored.

3.1 Verification Station: Chemical Biological Detection System

FIG. 4 provides a block diagram of the carrier security system deployed as either a verification station or a real time detection unit. The chemical and biological detection unit 410 analyzes the air and the elements within the detection area. The radioactive detection unit 408 analyzes the air and elements within the detection area. The filter port 412 provides an insertion point for the self-sealing filters obtained from static detection units. The processor 402 analyzes the inputs from the chemical, biological and radioactive detection units to determine if an alarm condition is present. The GPS antenna 418 connects the GPS processing within the local processor 402 to identify the current position of the carrier security system. The wireless antenna 416 provides connectivity for the data and video transmission unit located within the local processor 402. The wire-line connection provides connectivity for the data and video transmission unit located within the processor. A typical device would use either the wireless or wire-line communications options. The local alarm 414 provides audible and visual alarms. When a detection device 410, 408 detects a hazardous material, the local processor 402 recognizes the alarm, identifies the hazardous materials, quantifies the hazardous materials provides a local alarm and generates a local alarm message. The wireless or wire-line unit within the local processor sends an alarm message over the wireless or wire-line link 420, 416. The alarm data provides the GPS positioning obtained through the GPS antenna 418 and GPS processor 402, the hazardous material identification and measurement 410 and 408 the time and date and the carrier security system identification number. If the carrier security system is equipped with a video camera 404, digital video is transmitted to the monitoring station. If the carrier security system is equipped with a video recording device 406, video events are recorded.

An example of a Verification Station is the Chemical Biological Mass Spectrometer (CBMS). The CBMS is an ion trap mass spectrometer that is capable of biological agent detection.

The unit works by collecting an air sample, classifying it according to size, then heating it to break down its molecules. The sample is then moved into an ion trap mass spectrometer, where its mass-to-charge ratio and its chemical signature are compared against an extensive onboard library of known toxic agents, such as anthrax and VX gas.

The CBMS Block II is a compact, lightweight, rugged system capable of concurrent chemical and biological agent detection and identification. The system can identify all significant chemical agents (nerve, blister), in either liquid or vapor state, in less than 15 seconds and biological agents (ITF6A) at 25 ACPLA in less than 4 minutes. Its ion-trap configuration allows MS/MS analysis of samples that reduces false positives even in areas of high background. The system is designed to meet the vibration, temperature, and nuclear ruggedness requirements of military NBC reconnaissance systems. The CBMS Block II is easily maintainable and uses a minimum of consumables.

Figure 6:
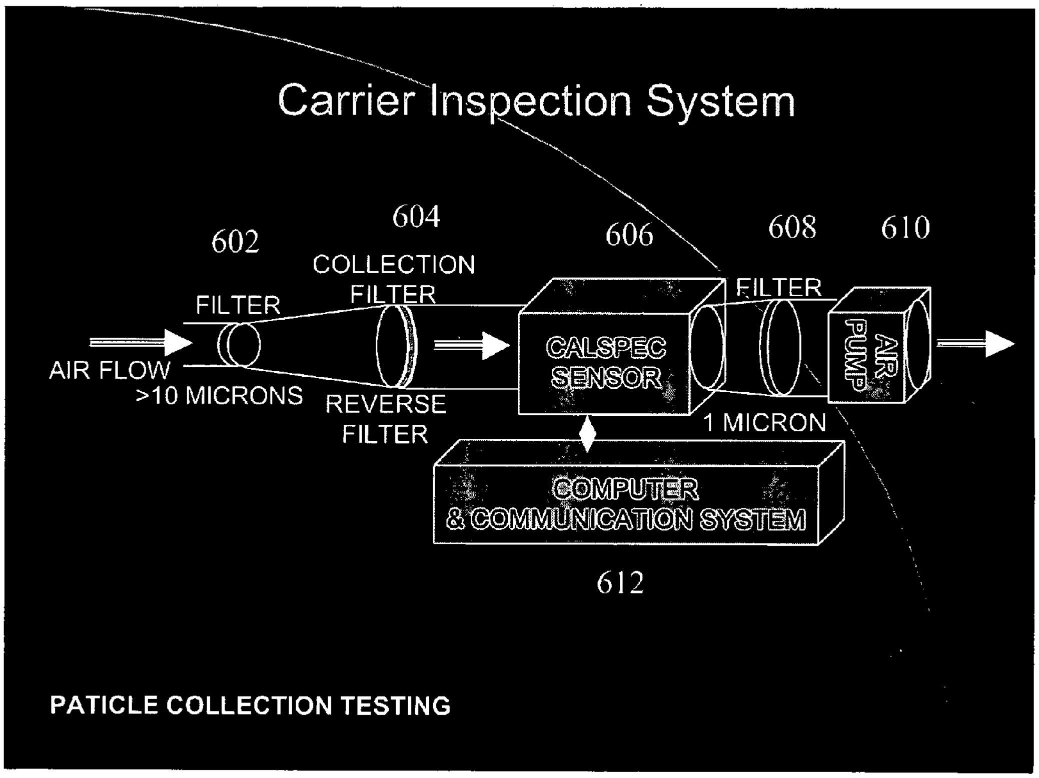
FIG. 6 is a block diagram showing a particle collector testing system according to a preferred embodiment of the present invention.

FIG. 6 provides a block diagram of the verification station used to test filters obtained from a static carrier security system. A filter 602 of a pre-determined value, such as 10 microns, clears elements from the air as the air is driven past the static filter that is placed in a reverse position 604. The collection filter is placed in a reverse position to drive the collected elements in to the sensor device 606. The sensor device could be a Calspec tester, a mass spectrometer, etc. The computer device 612 analyzed the output from the sensor 606 to detect, identify and measure the elements paced in the sensor device. The outer filter 608 traps the elements passing through the tester. The air pump 610 pulls the air through the system to enable the particles from the reverse filter 604 to be placed into the sensor. When a detection device 606 detects a hazardous material, the local processor 612 recognizes the alarm, identifies the hazardous materials, quantifies the hazardous materials provides a local alarm and generates a local alarm message. The communications device 612 sends an alarm message. The alarm data provides the GPS positioning, the hazardous material identification and measurement, the time and date and the carrier security system identification number.

3.2 Vehicle System

The static vehicle system uses an air handling unit and a filter trap to monitor the environment in the vehicle for hazardous materials. The filter traps materials from within the vehicle on a continuous basis. At selected intervals the self-sealing filter is removed and placed in a verification station to be tested for hazardous materials.

3.3 Collection Facility

The static collection facility system uses an air handling unit and a filter trap to monitor the environment in the collection facility for hazardous materials. The filter traps materials from within the collection facility on a continuous basis. At selected intervals the self-sealing filter is removed and placed in a verification station to be tested for hazardous materials.

3.4 Collection Box

The static collection box system uses an air handling unit and a filter trap to monitor the environment in the collection box for hazardous materials. The filter traps materials from within the collection box on a continuous basis. At selected intervals the self-sealing filter is removed and placed in a verification station to be tested for hazardous materials.

4.0 Processor

Processors are used to integrate subcomponents such as detection devices, communications equipment, GPS and video equipment. These processors are typically personal computers and/or brick computers.

5.0 Communication Device

A communications device is used in conjunction with the detection devices to transmit alarm data to a monitoring station. Example communications devices include wire-line, wireless Communications Systems and cellular communications.

6.0 Global Positioning System (GPS) Device

The GPS System collects satellite signals from the NAVSTARS satellite constellation; the constellation consists of 24 satellites, each having internal and external clocks; the GPS System has the ability to receive multiple signals from different satellites and geometrically calculates the position of the it; these operations and calculations can be performed once a second; the GPS System calculates the distance in fractions of seconds from the satellite to it, and with several satellites sending this signal the GPS System can be accurate down to 5–10 meters, but with the additional satellite or beacon correction, the GPS System is accurate to a matter of inches.

There are essentially two broad categories of GPS positioning which can be described as real-time navigation and high precision carrier phase positioning. Navigation uses a minimum of four pseudorange measurements to four satellites that are used to solve for the three-dimensional coordinates of the receiver and the clock offset between the receiver oscillator and GPS system time. An extension to this mode is differential GPS (DGPS) which again uses the pseudorange observable for positioning, but also incorporates real-time corrections for the errors inherent in the measurements.

The second category uses the much more precise carrier phase observations to compute baselines between two locations. Since the two carriers have short wavelengths (19 and 24 cm for L1 and L2 respectively), they cannot be used in the same manner as the pseudorange. The whole number of complete wavelengths (integer ambiguities) between the satellite and receiver must first be determined and this is carried out by post processing (static) or in Real-Time (RTK) using linear combinations of the two frequencies and differencing techniques.

Differences between these two modes are becoming less distinguishable. Combining the pseudorange with the phase data reduces the noise error within the pseudorange measurement resulting in a much higher positioning accuracy. New techniques are also being developed to solve for the integer ambiguities in a single epoch leading to very high baseline positioning in real-time. These are known as on-the-fly or fast ambiguity resolution techniques have already proved to provide accuracies of less than 1 cm on moving platforms over short baselines.

7.0 Local Alarms

Local alarms are provided to alert personnel of the potential contamination or the presence of hazardous materials. Local alarms are typically provided by means of contact points that change state when an alarm is generated. The contact points cause a light, buzzer or other activity to occur warning the personnel of the alarm.

8.0 Overview of Chemical and Biological Detection and Identification Processes

The effective detection of biological agents in the environment requires a multi-component analysis system because of the complexity of the environment. Other variables contributing to the effectiveness of detection of biological agents are the detection process itself and the efficient use of consumables in the field. Biological agent detection systems generally consist of four components: the trigger/cue, the collector, the detector, and the identifier. The function of these components is described in the remainder of this section, while section 8.1 will provide representative examples of each component.

Figure 5:
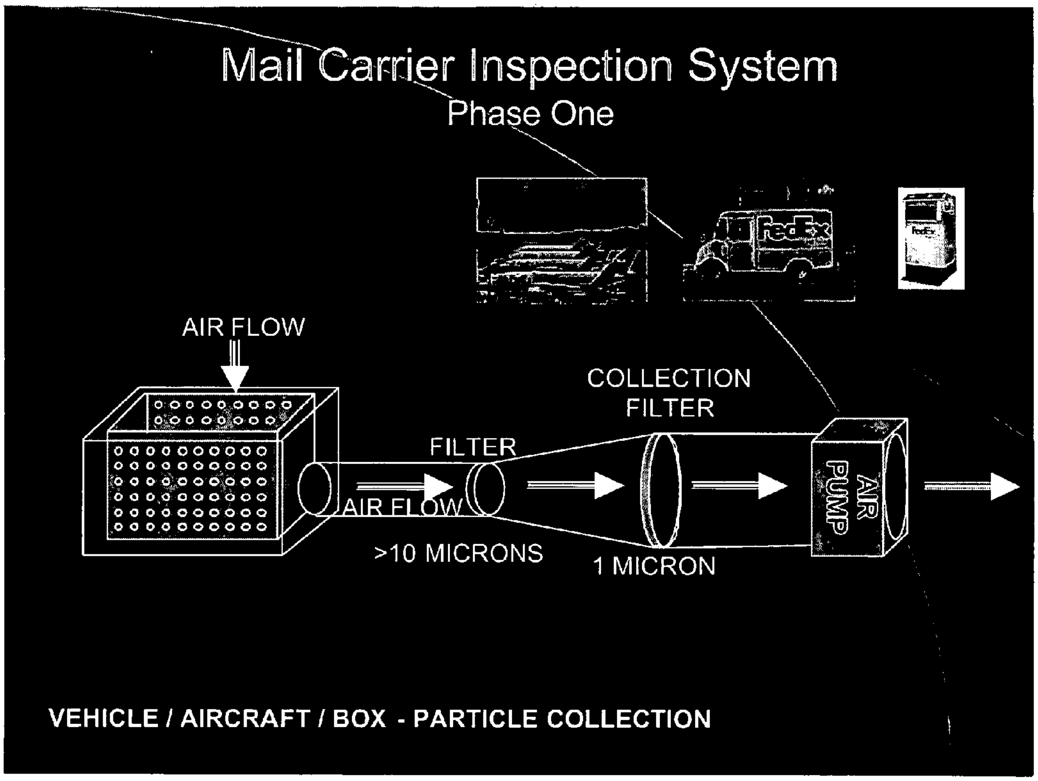
FIG. 5 is a block diagram showing a particle collection system according to a preferred embodiment of the present invention.

FIG. 5 provides a block diagram of the particle collection system used to provide samples for chemical and biological materials to be submitted to a verification system. A filter of a pre-determined value, such as 10 microns, 504 clears elements from the air handler unit 502. The collection filter 506 traps hazardous materials for analysis. The air pump 708 pulls the air through the system to enable the analysis.

Trigger technology is the first level of detection that determines any change in the particulate background at the sensor, indicating a possible introduction of biological agents. Detection of an increase in the particulate concentration by the trigger causes the remaining components of the detection system to begin operation. The trigger function typically provides a means of continuously monitoring the air without unnecessary use of consumables, thus keeping the logistical burden of biological agent detection low.

To reduce false positives (alarm with no biological agent) and false negatives (no alarm with agent), many detection systems combine trigger technology with a second detector technology (such as fluorescence that provides more selectivity) into a single technology known as cueing.

Most effective cueing technologies can detect airborne particulates in near real time and can discriminate between biological agent aerosol particles and other particles in air, avoiding unnecessary system activation. For example, a cueing device monitors the air for particulates, as does any other trigger device. When the particulate concentration increases, the cue determines if the particulates are biological in nature. The cue device generally uses a fluorescence detector to make this determination. If the particulates are found to be biological, the cue device activates the collector for sample collection.

8.1 Collector

Sampling of the biological agent is a crucial part of the identification system. The effective dose for some agents is extremely small; therefore, highly efficient collection devices must be employed. One type of collector pumps large volumes of air through a chamber where the air mixes with water. The water scrubs all the particulates from the air, resulting in a sample containing particulates suspended in water. Once collected in the water, the sample is further concentrated by evaporation of a portion of the water. After concentration, the sample moves into the analytical section of the biological agent detection system.

8.1.1 Samplers/Collectors

Since an extremely low airborne concentration of biological agents can be difficult to detect but still cause severe effects, a device to concentrate particles/aerosols in the air stream is needed. A collector/concentrator samples the atmosphere and concentrates the airborne particles into a liquid medium for analysis. Several types of samplers/collectors have been evaluated for biological agent detection. The principal differences between collection for biological agent detection and other types of aerosol or particulate sampling are (1) biological agent sampling is normally targeted at living organisms, so the sampling techniques must preserve and not harm the collected sample; (2) most biological detection and identification technologies require a liquid sample, so the collection must be from an aerosol or particulate in a liquid; and (3) the liquid sample must be highly concentrated and available for rapid analysis since response time is critical.

A collector is most useful when it is part of a detection system. When the collector receives a signal from a trigger indicating a change in the background level, an air sample is collected, and airborne particles are concentrated into a liquid medium.

The efficiency of a collector at capturing and concentrating aerosol samples typically affects several downstream functions. In virtually all systems, the collectors feed into the identification component of the biological detection system and also provide the samples that are used for confirmatory identification and forensic analysis.

Collectors can be broadly divided into two groups. One group contains collectors that are large and consume much power. These collectors, on the whole, have a high collection and concentration efficiency and are candidates for detection systems that operate well away from the line or point of agent release. The other group contains those collectors that consume little power, are hand-portable, and have relatively low collection and concentration efficiencies.

Whereas these collectors would work well in high agent concentrations (e.g., near the point or line of release, or perhaps indoors), they would fail to provide an adequate sample to downstream instruments. It should also be noted that collectors significantly contribute to the overall weight, size, and power requirements of a detection system. Examples of sampler/collector technologies include Viable Particle Size Samplers (Impactors), Virtual Impactors, Cyclones, and Bubblers/Impingers.

8.1.2 Viable Particle Size Samplers (Impactors)

A conventional impactor operates by accelerating an air stream of particles through a nozzle and diverting the air stream against an impaction plate maintained at a fixed distance from the nozzle. The larger particles are unable to Follow the fluid streamlines (air in this case) because of their large inertia; smaller particles follow the fluid streamlines and exit the sampler. The impactor usually has multiple stages and each stage contains a number of precision-drilled orifices that are a constant size for each stage. Particle laden air enters the instrument, and the airborne particles are directed towards the collection surfaces by the jet orifices. Any particle not collected by a specific stage follows the stream of air around the edge of the collection surface to he next stage. The collection plate is typically a petri dish with selective agar (selective to a specific organism). The plates are incubated (typically 24 h to 48 h) and after incubation, the number of colonies on each plate is counted.

8.1.3 Virtual Impactors

A virtual impactor is similar to a conventional impactor but uses a different impaction surface. The flat plate of the conventional impactor is replaced by a collection probe, and the larger particles penetrate the collection probe instead of striking a flat plate. By properly controlling the airflow in the impactor, it is possible to collect particles in a specific size range. In addition, the final stage can then aim the particle stream onto a liquid, resulting in a highly concentrated liquid sample. Power Engineering and Manufacturing, Inc manufactures the Liquid Sampler (PEM-0020) with carousel. The device uses virtual impaction to collect and concentrate airborne particles onto liquid film. The operator can select the number of samples to be collected (up to 10) and can choose from several preprogrammed sampling protocols that vary the volume and the collection time for each tube. Initiation of the sample collection is by external trigger or manual push button. The unit automatically repositions the carousel at the end of the collection cycle. The entire carousel can be quickly removed and replaced.

The BiOVIC™ Aerosol Collector, developed by MesoSystems Technology, Inc., serves as a front-end air sampler for biological detection systems. It is an impactor that preconcentrates the air stream, capturing large numbers of particles either into a small volume of liquid, into a small air stream, or onto a solid surface for delivery into the sensor. The BioVIC™ can be used with PCR, fluorescent-based optical sensors, mass spectrometry, pyrolysis GC mass spectrometry, or flow cytometry.

8.2 Chemical and Biological Detector/Identifier

Once a sample has been collected/concentrated, it must be determined if the particulates are biological or inorganic in origin. To accomplish this, the sample is passed to a generic detection component that analyzes the aerosol particles to determine if they are biological in origin. This component may also classify the suspect aerosol by broad category (e.g., spore, bacterium, toxin/macromolecule, or virus). In its simplest form, the detector acts as a "gateway" for further analysis. If the sample exhibits characteristics of biological particles, it is passed through to the next level of analysis. If the sample does not exhibit such characteristics, it is not passed to the next level of analysis, thereby conserving analytical consumables.

It is important to note that detection has traditionally taken place after the trigger function. For example, an aerosol particle sizer (APS) triggers, then a detector (e.g., flow cytometer) examines the aerosol for biological content. Many of the newer detection technologies combine the trigger and detection functionalities into a single instrument, creating a cueing instrument. The cue first detects a rise in particulates then determines if the particulates are of biological origin. If the sample is biological, the collector gathers a sample and passes it directly to the identifier.

An identifier is a device that specifically identifies the type of biological agent collected by the system. Identifiers are generally limited to a preselected set of agents and cannot identify agents outside of this set without the addition of new identifier chemistry/equipment or preprogramming. Because the identifier performs the final and highest level of agent detection, it is the most critical component of the detection architecture and has the widest variety of technologies and equipment available. The information obtained from the identifier is then used to determine protection requirements and treatment of exposed personnel.

8.2.1 Sample Chemical, Biological and Viral Detector and Identifier 8.2.1.1 Wet Detection (Flow Cytometry)

Cytometry is the measurement of both physical and chemical characteristics of cells. Flow cytometry (widely used as a wet detector for biological agents) uses the same technique as cytometry but makes the measurements of cells or other particles present in a moving fluid stream as they pass through a testing point. It measures particle sizes and counts particles in liquid suspensions through the use of laser light scattering. Flow cytometers involve sophisticated fluidics, laser optics, electronic detectors, analog to digital converters, and computers to provide an automated method for biochemical analysis and to process thousands of cells in a few seconds. Typically, the sample will also be treated by addition of a fluorescent dye that reacts with biological material (e.g., DNA). Flow cytometers have been commercially available since the early 1970s and increasingly have been used since then. Examples utilizing this technology are the Los Alamos National Laboratory Flow Cytometer (LANL) and the Becton Dickenson Flow Cytometer (FACSCaliber). They will be briefly discussed below.

The Los Alamos National Laboratory (LANL) Flow Cytometer employs a green (HeNe) laser diode. Particle size is measured by two light-scatter detectors, and fluorescence is measured by two photomultiplier tubes. This instrument is also known as the "Mini-Flow Cytometer" and is just 1.15 ft3 in size, 30 lb in weight, and requires 1 kW of power. The B-D Flow Cytometer FACSCount, manufactured by Becton Dickenson, employs a direct two-color immunogluorescence method and uses a green (HeNe) laser. The B-D Flow Cytometer FACSCaliber, manufactured by Becton Dickenson, is a four-color Modular Analytical Flow Cytometer that uses a 15 mW air-cooled blue argon-ion laser and a red laser diode. The FACSCalibur also has an optional sorter.

8.2.1.2 Dry Detectors (Mass Spectrometry)

Mass spectrometry (MS) is a microanalytical technique that requires only a few nanograms of analyte to obtain characteristic information on the structure and molecular weight of the analyte. The technique ionizes molecules and breaks them apart into characteristic fragments (the fragmentation pattern constitutes its "mass spectrum"). The mass spectrometer requires that samples be introduced in the gaseous state. Sample introduction into the mass spectrometer can be by direct air/gas sampling, a direct insertion probe, membrane inlets, effluent from a gas chromatograph (GC), effluent from a high-performance liquid chromatograph (HPLC), capillary electrophoresis, and effluent from pyrolysis devices. Several examples of detection equipment utilizing mass spectrometry are discussed below.

The Pyrolysis-Gas Chromatography-Ion Mobility Spectrometer (PY-GC-IMS) combusts, or pyrolyzes, the biological particles. The biological pyrolysis products are then separated using gas chromatography. Once separated, the individual pyrolysis products are introduced into an ion mobility spectrometer for analysis. This technology is still quite new and was developed in a collaborative effort between Edgewood Chemical Biological Center (ECBC) and the University of Utah.

The Matrix-Assisted Laser Desorption Ionization-Time of Flight-Mass Spectrometry (MALDITOFMS) is a variation of mass spectrometry that attempts to use a more gentle method of ionizing the suspect biological agent than pyrolysis to allow identification of the agent rather than just broad characterization.

Chemical Biological Mass Spectrometer (CBMS) uses a multistage process to analyze aerosols for biological content and categorize any biological constituents. The instrument first concentrates the aerosol, combusts or pyrolyzes it, then introduces the sample into a mass spectrometer for analysis. An on-board computer is used to analyze the mass spectra for patterns indicative of biological substances. The instrument is able to categorize biologicals as spores, cells, or toxins.

8.3 Identifiers (Specific Identification Technologies)

Identifiers are those components/instruments that are able to identify the suspect biological agent to the species level (for cellular and viral agents) and toxin type. Specific identification technologies determine the presence of a specific biological agent by relying on the detection of a specific biomarker that is unique for that agent. Antibody-based identifiers are used for systems where speed and automation are required. Where time and manpower are available, gene-based systems start to take the lead.

The technologies that are used to specifically identify a biological agent are the most critical components of the detection architecture. These components have the widest variety of technologies and equipment available.

8.4 CALSPEC Detection and Identification Device

To address the chemical detection and identification problem, we have focused primarily on absorption spectroscopy because spectroscopic information can provide essentially unambiguous selectivity from the unique spectral signature. In absorption spectroscopy, each element present in a sample absorbs different colors (wavelengths) of light from a source, and the resulting spectrum of nonabsorbed light-a series of bright and dark lines of different heights, widths, and colors-indicates which elements are present and in what amounts. A chemical compound like TNT, for example, has a specific signature; mercaptan odorants in methane and in propane in natural gas each have a different characteristic signature. We have developed and demonstrated several novel absorption spectroscopy techniques. In addition, we have developed promising miniature packaging schemes and fabrication approaches. Therefore, we believe that our development of microspectrometers provides the best compromise, providing high chemical specificity and sensitivity in a portable, compact package at a reasonably low cost for most applications.

Three different spectroscopic absorption techniques are demonstrated that could be used in a miniature instrument: dispersive spectroscopy (DS), Fourier Transform infrared (FTIR) spectroscopy, and calorimetric spectroscopy (CalSpec). The DS has a sensitivity of approximately one part per million (ppm). The dispersive microspectrometer can operate from the ultraviolet (UV) to the far-infrared (IR) part of the electromagnetic spectrum. It can operate in one of three modes to produce a unique spectral signature: emission, transmission, or reflection. In the emission mode, molecules are excited so they emit photons at particular wavelengths. In the transmission mode, atoms or molecules in the species preferentially absorb certain wavelengths of photons passing through the medium containing the target chemical species. Finally, in the reflection mode, certain wavelengths of photons reflected off a surface under investigation are preferentially absorbed, leaving a characteristic reflection spectrum.

The FTIR configuration provides an even higher sensitivity-one part per billion (ppb). FTIR spectroscopy is based on optical interferometry. A beam of photons from an IR source is split into two paths, with the first beam passing through the sample and later recombining with the second beam at an IR detector. Because the beams travel different distances before they reach the IR detector, they will constructively interfere at only a given wavelength. As the optical path for one of the beams is continuously changed (usually by moving a mirror), a complete interferogram is produced. The mathematical Fourier transform of the interferogram will result in a detailed infrared absorption spectrum of the molecules to be detected.

Finally, the CalSpec-based approach is a novel absorption spectroscopy technique that may allow us to reach detection limits of one part per trillion. Chemical and biological detection using CalSpec occurs in a two-step process. In the first step, the target molecules enter the device and are allowed to interact with, and adsorb onto, the surfaces of ultrasensitive micromechanical thermal detectors. These detectors sense the sample's changes in temperature as it absorbs photons from an IR source. In the second step, a calorimetric (photothermal) spectrum is obtained by scanning a broadband wavelength region with the aid of a monochromator, which disperses photons according to their wavelenths. For wavelengths at which the target molecules absorb incident photons, heat is generated, causing a temperature change in those particular thermal detectors. In response to these temperature changes, the detectors produce a photothermal spectrum that indicates that the target chemical has been detected and reveals its concentration in air.

Additional information can be obtained regarding the CalSpec device by reviewing U.S. Pat. No. 5,923,421, the entire teachings of which being hereby incorporated by reference.

9.0 Radioactive Detector Devices

Radioactive detection devices can be incorporated into the detection system to protect against such devices as dirty bombs. A variety of radioactive detection systems exist and can be incorporated into the system.

9.1 Sample Radioactive Detector

The following information describes a variety of radioactive detection systems that are currently available and that are under development.

9.1.1 Conventional Gamma Ray Detection Devices

The Radiant 200 Cadmium Telluride Spectroscopy System is a high performance thermoelectrically cooled portable x-ray and gamma ray spectroscopy system. Radiant 200 offers a combination of superior detection and spectroscopy characteristics. It exhibits very high sensitivity due to its large volume CdTe detector ($10\times10\times2$ $mm^3$) and its unique charge loss correction amplifier which provides improved spectral performance without throwing away counts. In addition it offers uncompromising energy resolution, which until recently was achievable only with cryogenically cooled systems.

The system includes a detector unit and power supply module. The device can operate autonomously using three L1 rechargeable batteries that can supply power for the whole system for up to 8 hours.

The detector unit consists of the detector head, charge-sensitive preamplifier and temperature stabilization system, which compensates for varying ambient temperature. The detector head includes our high performance CdTe detector and a preamplifier module, both mounted on a Peltier cooler. It features a conical shape, which allows the detector to be placed in close proximity to the sample for optimal collection and to collect from hard-to-reach spots.

9.1.2 Advanced and Miniature Radioactive Detectors

Gallium arsenide detectors have been under development as neutron detectors for several years at Argonne National Laboratory and the University of Michigan. Novel new detectors have been fabricated which exhibit marked improvement in the detection efficiency for thermal neutrons. The novelty of the design is based on etching minute holes in the surface of the semiconductor, which forms a matrix of via holes over the surface. Contacts are then deposited on the rough surface and the holes are filled with enriched boron.

In many nuclear applications, detection of neutrons in harsh environments is often vital to the project. These harsh environments include high radiation fields (i.e. weapons and fissile material detection and characterization), field operations (where size, portability, and durability are essential), high vacuum operations (i.e. physics or space applications), or a variety of other environmental considerations.

Gallium arsenide (GaAs) detectors with various surface coatings are being developed to provide improved neutron detectors with a wide range of potential applications. These detectors are small (1 $cm^2$ or smaller), low power (50 volts, 10 nano-amps), low cost (fabricated using semi-conductor manufacturing techniques), and radiation resistant. Variations in the type of surface coating can provide sensitivity over a range of neutron energies from thermal to fast (14 MeV) while still providing an excellent discrimination capability against background gamma radiation. The use of recoil particles from neutron interactions within the surface coating gives the detectors intrinsic directional sensing capability. It is also possible to create large relatively inexpensive arrays of these detectors using semiconductor manufacturing techniques.

Gallium arsenide is a semi-conductor material that acts like silicon. However, GaAs Schottky devices can withstand relatively high radiation fields and operate at room temperature with low leakage currents. Detectors are fabricated from GaAs wafers using conventional microchip processing techniques. Coatings are applied to the surface of the wafer to convert incident neutrons into charged particles. The detector response can be varied based on the coatings applied. For example, $^{10}B$ is used to detect thermal neutrons via the $^{10}B(n,\alpha)^{7}Li$ reaction, and plastics are used to detect fast neutrons via proton recoils in the hydrogenous material.

When a small voltage is applied across the GaAs wafer, a truncated high field or active region is produced near the contact. The incident neutrons are converted into charged particles in the coating, i.e. recoil protons in the figure, which excite free charge carriers in the GaAs detector active region.

The charge carriers drift to the detector contacts, and a preamplifier circuit measures the induced charge. Charges excited in the low field or substrate region are not collected. In addition, because the active region is so thin (10–20 $\mu$m), background gamma-ray interactions are reduced. Gamma rays that interact in the active region are easily discriminated from the recoil protons.

The GaAs detectors are versatile and offer distinct advantages over other detector types. Several concepts have been developed which employ coated GaAs detectors for neutron detection for a broad range of applications. Some of these applications are described below.

Fissile materials emit characteristic and identifying radiation. Gamma ray emissions are discreet, and special nuclear materials (SNM) can be identified simply by the gamma ray energies that are detected. Yet, gamma ray emissions can be easily shielded, and many natural sources do emit gamma rays of similar energies. Neutron emissions are much more suspect, in that relatively few isotopes undergo spontaneous neutron emissions. Those that do are mostly controlled substances.

Neutron detection is generally performed by second order effects—a neutron reacts through either absorption or scattering within a medium thereby producing detectable byproducts. Thermal neutrons can be detected with a variety of absorption reactions, the most common being the $^{10}B(n,\alpha)$ $^{7}Li$, the $^{6}Li(n,\alpha)^{3}H$, and the $^{3}He(n,p)^{3}H$ reactions. These reactions, however useful, all demonstrate a 1/v cross section dependence, and their reaction cross sections are comparably low for neutrons of energies approaching 1 MeV.

11.0 Video Surveillance Equipment

Video equipment is used to support remote video surveillance and digital video recording capabilities. The following equipment provides an example of the devices that can be used in the system.

Devices such as the PelcoNet™ provide an easy-to-use, all-in-one solution that allows users to view real-time video over Local Area Network (LAN) and even Wide Area Networks (WAN). Security professionals can view digital video on any standard CCTV monitor or on a PC using popular web browser software. With PelcoNet, all the video security equipment—with video, audio and complete p/t/z control—can be easily and cost effectively integrated into existing digital network systems.

Devices such as the DX1000 Series Digital Video Recorder (DVR) is a high-quality compact recorder that combines the functions of a recorder and multiplexer into one unit. Having no tapes to maintain, replace, or rewind means that this recorder can be set up once and virtually forgotten about until and unless a review of the video becomes necessary. It also dramatically reduces the down time for maintenance or repair that is generally associated with VCRs.

Devices such as the Spectra III Series Discreet Video Security Positioning System BY Pelco is an integrated dome/camera system for the video security industry. Spectra III SE offers many innovative features and technologies that greatly expand the benefits of using integrated dome systems. New memory storage and data transfer technologies, window-blanking features, and breadth of this line make Spectra III a perfect fit for a wide range of applications.

12.0 Exemplary Processes

Figure 9:
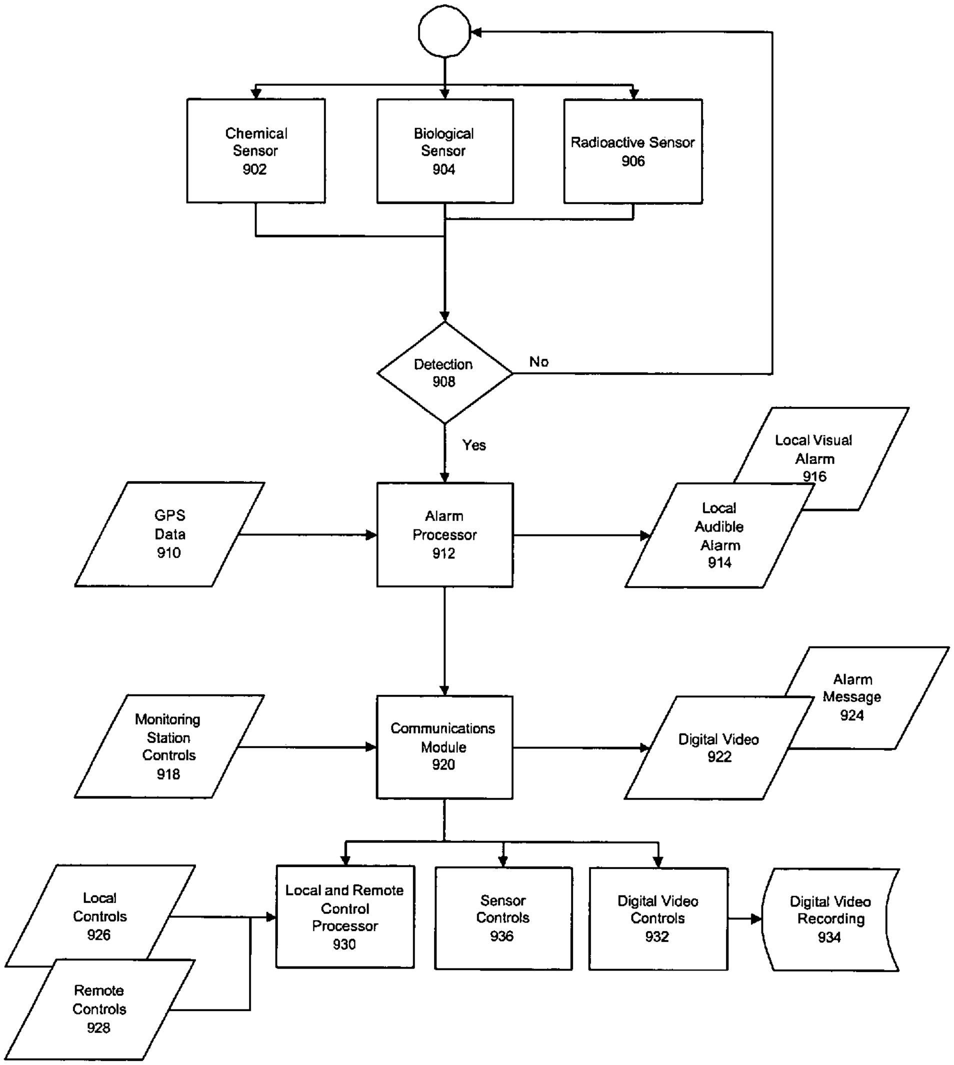
FIG. 9 is a flow chart showing exemplary processes used in a carrier detection system as described in a preferred embodiment of the present invention.

Referring to FIG. 9, chemical sensors 902, biological sensors 904, and radioactive sensors 906 are monitoring for detection of hazardous materials. When a hazardous material is detected the alarm processor generates local alarms 914, 916. The alarm processor obtains GPS data 910 and the communications module 920 generates an alarm message 924 and sends the alarm message to the monitoring station. The communications module also sends digital video 922 to the monitoring station if the camera option is available. The monitoring station communicates with the detection system 918, 928, 920 and provides remote controls 930. Local controls can be used to interact with the detection system 926. Sensor controls 936 and video controls can be activated from local 926 or remote controls 928.

Figure 10:
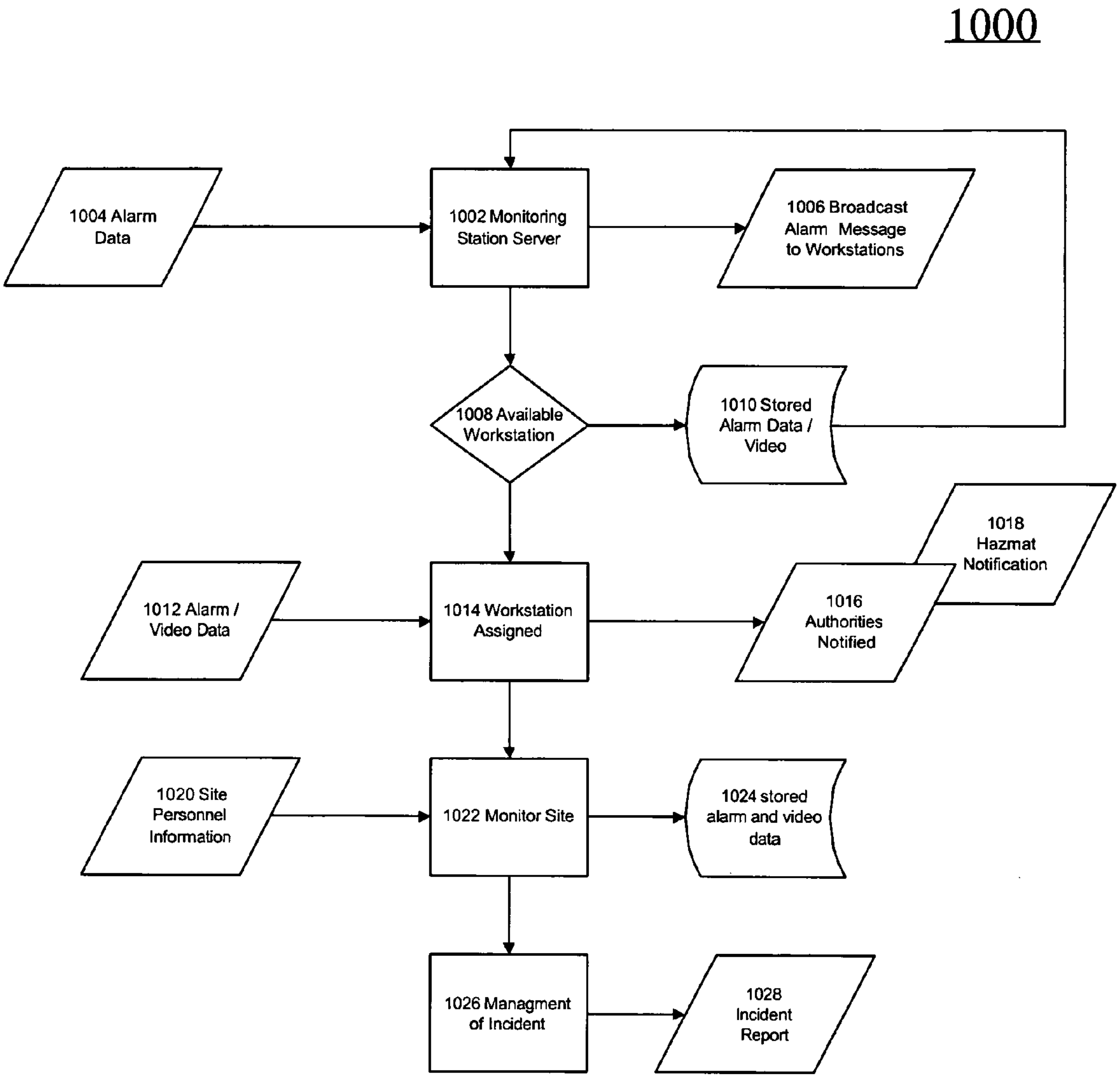
FIG. 10 is a flow chart showing exemplary processes used in a monitoring station as described in a preferred embodiment of the present invention.

In FIG. 10, the monitoring station receives an alarm message 1004 from the carrier detection system. The message is received by the monitoring station server 1002. The server searches for an available work station 1008. If an available workstation is found the alarm is assigned 1014. If there is no available workstation at that time the server begins to save all data associated with the alarm 1010 and continue to search for an available workstation.

When the workstation is assigned the alarm data is forwarded to the workstation 1012. The workstation analyzes the alarm and notifies proper authorities of the event 1016 and notifies the HAZMAT team 1018.

Workstation personnel contact the site personnel 1020 and gather additional information. The workstation personnel continue to monitor the site 1022 and store the alarm data 1024. The workstation personnel manage the incident until closure and complete incident reports 1028.

13.0 Exemplary Alarm Messages

Figure 12:
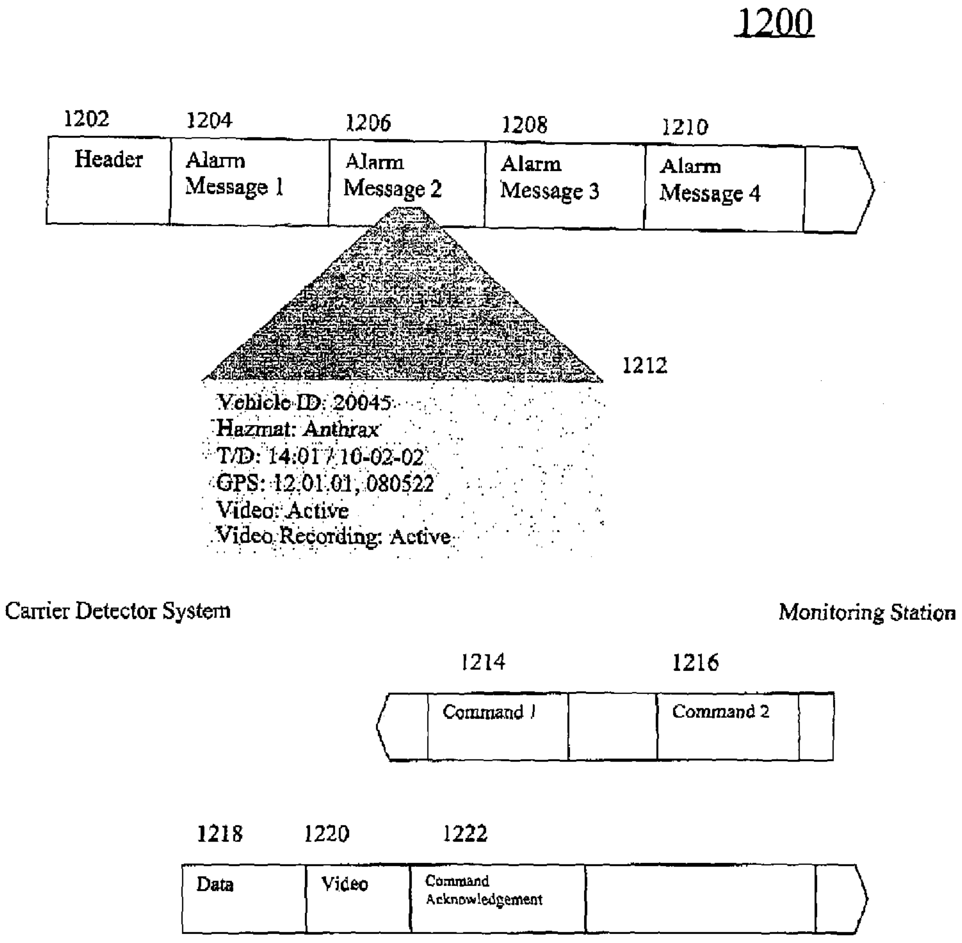
FIG. 12 is a chart showing examples of messages that are passed between the carrier detection systems and the monitoring station as described in a preferred embodiment of the present invention.

FIG. 12 provides an example of the messages and commands that are passed between the monitoring station and the carrier detection system. A typical alarm message 1206 would be sent to the monitoring station to alert the monitoring station that a hazardous material has been detected. Item 1212 provides an example of the types of information that could be found in an alarm message.

The monitoring station could send commands 1214 to the carrier detection system to shut off the local alarms, to move the camera, to download stored video or alarm data, etc. The carrier detection system would respond to the commands providing an acknowledgement 1222 and act upon the commands by sending data 1218 or video 1220 or moving the camera, etc.

The preferred embodiments of the present invention can be realized in hardware, software, or a combination of hardware and software. A system according to a preferred embodiment of the present invention can be realized in a centralized fashion in one computer system, or in a distributed fashion where different elements are spread across several interconnected computer systems. Any kind of computer system—or other apparatus adapted for carrying out the methods described herein—is suited. A typical combination of hardware and software could be a general purpose computer system with a computer program that, when being loaded and executed, controls the computer system such that it carries out the methods described herein.

A preferred embodiment according to present invention can also be embedded in a computer program product, which comprises all the features enabling the implementation of the methods described herein, and which—when loaded in a computer system—is able to carry out these methods. Computer program means or computer program in the present context mean any expression, in any language, code or notation, of a set of instructions intended to cause a system having an information processing capability to perform a particular function either directly or after either or both of the following a) conversion to another language, code or, notation; and b) reproduction in a different material form.

Each computer system may include one or more computers and at least a computer readable medium allowing a computer to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer medium may include, for example, volatile storage such as RAM, buffers, cache memory, and network circuits. Furthermore, the computer readable medium may comprise computer readable information in a transitory state medium such as a network link and/or a network interface, including a wired network or a wireless network, that allow a computer to read such computer readable information.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A carrier security system comprising:

an element detection system for automatically, continuously, and autonomously, detecting, comprising detecting by calorimetric spectroscopy at least one biological hazardous element and without using chemical reagents, at least one unauthorized element in a carrier storage environment for containing at least one delivery item, and wherein the element detection system includes an impactor that collects particles for the detecting by the element detection system;

a computer system communicatively coupled to the element detection system, the computer system being responsive to the element detection system automatically detecting the at least one unauthorized element for communicating detected element information from the element detection system to the computer system for automatically detecting at least one unauthorized element in the carrier storage environment and determining an alarm condition; and an alarm notification system communicatively coupled to the computer system for generating an alarm notification signal in response to the computer system determining an alarm condition.

2. The carrier security system of claim 1, further comprising at least one remote monitoring station, being communicatively coupled with the computer system, for remotely monitoring the alarm condition determined by the computer system.

3. The carrier security system of claim 2, wherein the at least one remote monitoring station is communicatively coupled with the computer system by at least one of a wired link and a wireless link.

4. The carrier security system of claim 1, wherein the element detection system is suitable for detection of the following: a chemical hazardous element, a biological hazardous element, a radioactive hazardous element, and an explosive hazardous element.

5. The carrier security system of claim 1, further comprising a video information capture system, communicatively coupled to the computer system, for capturing video information of the carrier storage environment containing delivery items, and wherein the computer system determining an alarm condition further associates any captured video information with the alarm condition for providing the captured video information to personnel.

6. The carrier security system of claim 5, further comprising at least one remote monitoring station, being communicatively coupled with the computer system, for remotely monitoring the alarm condition determined by the computer system.

7. The carrier security system of claim 6, wherein, in response to the computer system determining the alarm condition, the at least one remote monitoring station remotely receives the captured video information associated with the alarm condition for providing the captured video information to remote monitoring station personnel.

8. The carrier security system of claim 1, wherein the element detection system comprises:

a static detection system for collecting samples of air in the carrier environment in order to detect at least one unauthorized element; and a verification station, communicatively coupled to the static detection system, the verification station for monitoring the collected air samples from the static detection system and identifying the at least one unauthorized element.

9. The carrier security system of claim 8, wherein the static detection system comprises:

an air handler for circulating the air in the carrier environment; and a self-sealing filter for trapping particles of the at least one unauthorized element and allow removal of the filter without contamination from the at least one unauthorized element.

10. The carrier security system of claim 9, wherein the verification station comprises at least one of an ion trap mass spectrometer and a radioactive detection device.

11. The carrier security system of claim 10, wherein the radioactive detection device comprises at least one of a gamma ray detection device, an x-ray detection device, and a neutron detection device.

12. The carrier security system of claim 8, wherein the verification station identifies the at least one unauthorized element by calorimetric spectroscopy.

13. The carrier security system of claim 12, wherein the verification station comprises a CalSpec tester for detecting the at least one unauthorized element at a sensitivity of substantially one part per trillion.

14. The carrier security system of claim 1, further comprising:

a means for automatically moving the element detection system throughout the carrier storage environment.

15. The carrier security system of claim 1, wherein the element detection system further for automatically, continuously, and autonomously, detecting at least one radioactive hazardous element.

16. The carrier security system of claim 1, wherein the element detection system includes a virtual impactor that collects particles for the detecting by the element detection system.

17. A carrier vehicle security system comprising:

an element detection system for automatically, continuously, and autonomously, detecting, comprising detecting by calorimetric spectroscopy at least one biological hazardous element and without using chemical reagents, at least one unauthorized element in a carrier vehicle environment for containing at least one delivery item, the element detection system further for detecting at least one chemical hazardous element, and wherein the element detection system includes an impactor that collects particles for the detecting by the element detection system;

a computer system communicatively coupled to the element detection system, the computer system being responsive to the element detection system automatically detecting the at least one unauthorized element for communicating detected element information from the element detection system to the computer system for automatically detecting at least one unauthorized element in the carrier vehicle environment and determining an alarm condition; and an alarm notification system communicatively coupled to the computer system for generating an alarm notification signal in response to the computer system determining an alarm condition.

18. The carrier vehicle security system of claim 17, further comprising at least one remote monitoring station, being communicatively coupled with the computer system, for remotely monitoring the alarm condition determined by the computer system.

19. The carrier vehicle security system of claim 18, wherein the at least one remote monitoring station is communicatively coupled with the computer system by at least one of a wired link and a wireless link.

20. The carrier vehicle security system of claim 18, wherein the at least one remote monitoring station comprises an alarm condition notification system for notifying remote monitoring station personnel that an alarm condition has been determined by the computer system of the carrier vehicle security system.

21. The carrier vehicle security system of claim 17, wherein the element detection system is suitable for detection of the following: a a radioactive hazardous element and an explosive hazardous element.

22. The carrier vehicle security system of claim 17, further comprising a video information capture system, communicatively coupled to the computer system, for capturing video information of the carrier vehicle environment containing delivery items, and wherein the computer system determining an alarm condition further associates any captured video information with the alarm condition for providing the captured video information to personnel.

23. The carrier vehicle security system of claim 22, further comprising at least one remote monitoring station, being communicatively coupled with the computer system, for remotely monitoring the alarm condition determined by the computer system.

24. The carrier vehicle security system of claim 23, wherein, in response to the computer system determining the alarm condition, the at least one remote monitoring station remotely receives the captured video information associated with the alarm condition for providing the captured video information to remote monitoring station personnel.

25. The carrier vehicle security system of claim 17, wherein the alarm notification signal comprises at least one of a visual indication and an audible indication of the determined alarm condition.

26. The carrier vehicle security system of claim 17, further comprising a global positioning system, communicatively coupled to the computer system, for locating a position of the carrier vehicle environment containing delivery items, and wherein the computer system determining an alarm condition further associates any global positioning information with the alarm condition.

27. The carrier vehicle security system of claim 17, wherein the element detection system comprises a CalSpec tester for detecting the at least one unauthorized element comprising detecting the at least one biological hazardous element.

28. The carrier vehicle security system of claim 27, wherein the CalSpec tester for detecting the at least one unauthorized element at a sensitivity of substantially one part per trillion.

29. A method comprising the steps of:

automatically, continuously, and autonomously, monitoring the air in a carrier storage environment for containing at least one delivery item;

automatically, continuously, and autonomously, detecting, comprising detecting by calorimetric spectroscopy at least one biological hazardous element and without using chemical reagents, at least one unauthorized element in the carrier storage environment;

particle collection by an impactor, wherein collected particles being used by the detecting of the at least one unauthorized element;

capturing information relating to the at least one unauthorized element from the element detection system;

automatically determining, from the captured information, an alarm condition; and generating an alarm notification signal in response to determining an alarm condition.

30. The method of claim 29, wherein the automatically, continuously, and autonomously, detecting the at least one unauthorized element further comprising detecting for: a chemical hazardous element, a a radioactive hazardous element, and an explosive hazardous element.

31. The method of claim 29, further comprising associating any captured video information of the carrier storage environment with the alarm condition.

32. The method of claim 29, wherein the alarm notification signal comprises at least one of a visual indication and an audible indication of the determined alarm condition.

33. The method of claim 29, wherein the automatically, continuously, and autonomously, detecting comprises detecting the at least one unauthorized element by calorimetric spectroscopy.

34. The method of claim 29, wherein the automatically, continuously, and autonomously, detecting is done with a CalSpec tester for detecting the at least one unauthorized element at a sensitivity of substantially one part per trillion.

35. A computer readable medium comprising computer instructions for performing the steps of:

automatically, continuously, and autonomously, monitoring the air in a carrier storage environment for containing at least one delivery item;

automatically, continuously, and autonomously, detecting, comprising detecting by calorimetric spectroscopy at least one biological hazardous element and without using chemical reagents, at least one unauthorized element in the carrier storage environment;

particle collection by an impactor, wherein collected particles being used by the detecting of the at least one unauthorized element;

capturing information relating to the detected at least one unauthorized element from the element detection system;

automatically determining, from the captured information, an alarm condition; and generating an alarm notification signal in response to determining an alarm condition.

36. The computer readable medium of claim 35, wherein the automatically, continuously, and autonomously, detecting the at least one unauthorized element further comprising detecting for: a chemical hazardous element, a radioactive hazardous element, and an explosive hazardous element.

37. The computer readable medium of claim 35, further comprising computer instructions for associating any captured video information of the carrier storage environment with the alarm condition.

* * * * *

UNITED STATES PATENT AND TRADEMARK OFFICE

CERTIFICATE OF CORRECTION

PATENT NO. : 7,005,982 B1
APPLICATION NO. : 10/280255
DATED : February 28, 2006
INVENTOR(S) : Frank It is certified that error appears in the above-identified patent and that said Letters Patent is hereby corrected as shown below:

On title page Item (57)
In the Abstract, line 12, please delete “carriers”, and insert - - services - - ;

Column 22, line 13, delete “a a radioactive”, and insert - - a redioactive - -

Signed and Sealed this

First Day of August, 2006

JON W. DUDAS
*Director of the United States Patent and Trademark Office*